United States Patent [19]

Backscheider et al.

[11] Patent Number: 4,963,134
[45] Date of Patent: Oct. 16, 1990

[54] LASER SURGERY PLUME EVACUATOR WITH ASPIRATOR

[75] Inventors: Frank A. Backscheider, Batavia; Paul Rogers, Cincinnati, both of Ohio

[73] Assignees: United States Medical Corporation; Recto Molded Products, Inc., both of Cincinnati, Ohio

[21] Appl. No.: 319,121

[22] Filed: Mar. 3, 1989

[51] Int. Cl.$^5$ ............................................. A61M 1/00
[52] U.S. Cl. .................................. 604/319; 55/316; 55/387; 55/467; 55/279
[58] Field of Search .................. 55/279, 473, 316, 467, 55/387, 356, 357; 604/317, 319, 405, 410

[56] References Cited

U.S. PATENT DOCUMENTS

| | | | |
|---|---|---|---|
| 1,266,228 | 5/1918 | De Vilbiss | 128/200.14 |
| 2,173,637 | 9/1939 | Riedener | 128/760 |
| 3,526,219 | 9/1970 | Balamuth | 128/2 |
| 3,939,515 | 2/1976 | Platek | 15/321 |
| 3,982,541 | 9/1976 | L'Esperance, Jr. | 128/303.1 |
| 4,176,453 | 12/1979 | Abbott | 433/82 |
| 4,207,874 | 6/1980 | Choy | 128/6 |
| 4,402,310 | 9/1983 | Kimura | 128/4 |
| 4,487,606 | 12/1984 | Leviton et al. | 55/385.4 |
| 4,516,398 | 5/1985 | Wuchinich | 604/22 |
| 4,531,934 | 7/1985 | Kossovsky et al. | 604/22 |
| 4,562,838 | 1/1986 | Walker | 128/303.14 |
| 4,617,013 | 10/1986 | Betz | 604/39 |
| 4,619,672 | 10/1986 | Robertson | 55/316 |
| 4,648,386 | 3/1987 | Morritt et al. | 128/4 |
| 4,694,828 | 9/1987 | Eichenbaum | 128/303.1 |
| 4,731,224 | 3/1988 | Kawashima | 55/279 |
| 4,735,603 | 4/1988 | Goodson et al. | 604/21 |
| 4,737,173 | 4/1988 | Kudirka | 55/316 |
| 4,810,269 | 3/1989 | Stackhouse et al. | 55/356 |
| 4,826,513 | 5/1989 | Stackhouse et al. | 55/316 |
| 4,857,063 | 8/1989 | Glenn | 604/317 |

FOREIGN PATENT DOCUMENTS 3418341 11/1985 Fed. Rep. of Germany ...... 604/319

OTHER PUBLICATIONS

LASE System II Maintenance/Service Manual (LASE, Inc.).
Brochure entitled "Introducing Clean Air" (LASE, Inc.).

Primary Examiner—Bernard Nozick
Attorney, Agent, or Firm—Wood, Herron & Evans

[57] ABSTRACT

A portable laser surgery evacuator includes an aspirator contained in the same housing which is positionable in an operating room near a surgical site. Surgical plume is evacuated from the site by vacuum, filtered through moisture, purifying and particle filters, chemically deodorized, and exhausted in cleaned form into the operating room environment. Fluid containing liquid is aspirated by pumping to a collector bag hung on a hose of the evacuator. Gaseous plume components of the fluid are vented from the collector to the evacuator to be cleaned with the plume. The venting is provided by a hose joining the evacuator inlet hose at a Venturi like connection. The evacuator includes a symmetrical reversible charcoal filter having a moisture absorbing cellulose filter at each end. A disposable aspirator pump of the rotating impeller type mounts on a motor shaft extending through the housing and is restrained against rotation by fixed hooks against which the pump fittings are urged by the torque of the motor.

31 Claims, 3 Drawing Sheets

LASER SURGERY PLUME EVACUATOR WITH ASPIRATOR

BACKGROUND OF THE INVENTION

I. Field of the Invention

The present invention relates to evacuation apparatus for removing laser smoke from the operative site during laser surgery. More specifically, the present invention relates to evacuation and suction apparatus for evacuating the gaseous plume of smoke and vapor products of laser surgery as well as liquid material from the operating field.

II. Description of the Prior Art

Laser surgery is becoming an increasingly useful and preferred surgical procedure. For example, laser surgery has been used to remove human tumors and the like. In the laser surgical process, the surgeon applies a highly concentrated beam of coherent light to the surgical site to both cut and cauterize the tissue. The process burns, chars and partially vaporizes the tissue. Laser surgery is preferred to reduce the extent and duration of surgery and to induce better healing of the operative incision. Nonetheless, the burning process of laser surgery is known to generate an offensive and undesirable cloud of particulate laden smoke and vapor referred to as the plume. This plume contains degradation products of tissue charred or burned by exposure to the intensely concentrated energy of the laser beam. The plume generated during laser surgery, if allowed to remain at the operative site, tends to cloud the surgeon's view and to fill the environment of the operating room with plume contaminants. The contaminants may be unsafe and are offensive to the patient and to the physicians, nurses and others attending the surgery.

To accommodate this plume problem, evacuator systems have been developed by which the plume may be withdrawn from the operating field before it escapes into the environment of the operating room. Such an evacuator system typically includes a source of vacuum coupled to a vacuum hose, the nozzle of which is positioned adjacent the operative site to suction the plume away. The evacuator often further includes a series of filters or the like to remove the particulate matter and vapors from the plume as it passes from the vacuum hose into the evacuator unit so that the cleansed air may be exhausted back into the environment of the operating room. An example of such an evacuator is the Lase System II available from U.S. Medical Corporation in Cincinnati, Ohio. The Lase System II was previously available from Lase Inc. in Cincinnati, Ohio. Lase Inc. merged with U.S. Medical Corporation.

While laser plume evacuators are beneficial, such systems are not always sufficient to clear the operative site. In particular, the operative site typically also contains a substantial amount of liquid such as blood or other bodily fluids. Suction of the liquid by the evacuator tends to clog the filters reducing their efficiency and requiring their frequent replacement. Moreover, the evacuator is not equipped to completely and efficiently remove such liquids which may result in fluids accumulating at the operative site.

One proposed solution to the liquid accumulation or removal problem has been to utilize aspirator suction lines conventionally provided at a hospital facility to remove the liquid from the operating room. The built-in hospital aspiration system usually includes a series of suction lines plumbed into the hospital building which may be used during surgery to aspirate the liquid from the operative site. The liquid so removed is to be transported through the fixed plumbing pipes and disposed of at a central location. However, use of a hospital aspiration suction system has serious drawbacks.

The aspirator suction tends to draw off plume as well as liquids. The plume includes tar like components which have a tendency to deposit and accumulate in the plumbing of the hospital aspirator suction lines. Consequently, the aspirator system may eventually foul in which event it may become necessary to tear open the wall of the building to reach the plumbing and replace clogged pipes from time to time.

Where the hospital aspiration system is used to remove both the plume and surgical liquids, the problem is quite aggravated. In this situation, the hospital suction system may clog very rapidly. Further, the suction of the hospital aspiration line is typically not able to draw off all of the plume created during laser surgery. Hence, the operative site may become clouded and/or plume may escape into the operating room environment. Thus, use of an evacuator system along with the hospital aspiration system is the better approach. Even with both the evacuator and hospital aspirator systems, however, clogging is not entirely avoided because the aspiration system tends to draw off some of the plume. Moreover, use of the hospital aspirator to remove primarily liquids, along with the use of an evacuator to remove plume smoke and vapors, is not always an available solution.

For example, laser surgery may be performed in an outpatient clinic or doctor's office environment where built-in aspiration systems are not practical. Portable aspiration systems may be available for this purpose, but they may be subject to clogging as well. In situations where a portable evacuator system and a portable aspiration system are both available, they may require operating room space and separate power sources and thus represent an inconvenience to those attending the surgury. Still further, reuse of portions of a portable aspiration system for subsequent operations presents a sterility management problem.

An even greater drawback to use of a hospital or portable aspiration system is not merely clogging of the system, but that the aspiration system will draw off some amount of plume which will subsequently be discharged, typically untreated, into the environment. Typically, liquid suctioned from the operative site may be collected in a container. To prevent overpressuring of the container, gases which tend to accumulate in the container may be vented to atmosphere. Under these circumstances, plume which enters the aspirator system will often collect in the liquid collection container and then be vented to atmosphere. Thus, some plume would bypass the evacuator filters and the release of some of the obnoxious plume vapors into the air will occur. This is most undesirable, particularly if a portable aspiration unit is employed in the operating room in which event the plume vapors may be released directly back into the operating room.

SUMMARY OF THE INVENTION

The present invention provides a portable and self-contained system which will effectively remove both plume and liquid from a laser surgery operative site. The present invention further provides a system which substantially reduces plume exhaust to the environment from aspiration of liquids during laser surgery. The present invention further provides an evacuator and aspirator system which facilitates rapid and error free change of clogged, spent or used components of the system. Still further, the present invention provides such a system in which sterility management is facilitated.

In accordance with the principles of the present invention, and in one of its aspects, there is provided a single portable unit which contains both a vacuum filtration system for plume evacuation and an aspirator pump system for liquid aspiration. More particularly, an evacuation hose may be coupled to the vacuum filtration system and the nozzle placed adjacent the operative site for evacuating the plume developed during laser surgery. Simultaneously, an aspirator tube may be coupled to the aspirator pump system and the nozzle thereof also positioned adjacent the operative site so as to draw away liquid such as blood or other bodily fluids. Both the evacuator and aspirator are thus contained within a single housing and may be powered by the same power source with less inconvenience to those attending the surgeon. The present invention further provides the advantage of eliminating the need to rely upon a built-in or other hospital system for aspiration.

In accordance with a further aspect of the present invention, the aspirator pump system is comprised of a motor built into and contained within the housing of the unit and a replaceable impeller pump unit outboard of the unit. In particular, the motor includes a rotatable output shaft extending from the housing and over which the replaceable impeller pump unit may be slidably mounted. Coupled to the impeller pump unit is the aspirator tube so that the impeller pump unit and aspirator tube are easily removed and replaced after each surgery thereby providing a greater level of sterility management. Further, should the impeller pump or the related tube become clogged, the aspirator tube and/or impeller pump may be readily disposed of and replaced with a new pump and/or section of tube.

To aid in the efficient and rapid change of the impeller pump unit, the impeller pump is made to be fully supported on the pump motor shaft and held in place and against rotation by the torque of the pump motor, thus eliminating the need of operating room personnel to use and manipulate fasteners to hold the pump in place. This is preferably accomplished by providing fixed hooks on the apparatus housing which engage inlet and outlet tube connectors on the impeller pump unit to both prevent it from rotating and to hold it to the housing.

The present invention further provides means for reducing or eliminating the expelling of untreated plume into the environment from the aspirator pump assembly. In accordance with this further aspect of the invention, the vacuum filtration and aspirator pump assemblies are interconnected in such a way that any plume drawn off by the aspirator pump assembly and not contained therein is caused to be passed through the vacuum filtration assembly of the evacuator system before being vented to atmosphere. In particular, the outlet of the aspirator pump assembly feeds the aspirant collected from the operative site into a container which is then vented directly to the evacuator hose so that plume escaping through the aspirator system is fed back into the intake of the vacuum filtration assembly where the drawn off plume is filtered through the filters of the vacuum filtration assembly before being exhausting into the environment. In a preferred embodiment, the container is a plastic bag with a plastic filter membrane dividing the bag into two halves, one half communicating directly with the aspirator pump outlet, the other half communicating directly with the vacuum filtration assembly.

Thus, the present invention provides a portable self-contained laser surgery plume evacuator and liquid aspirator system by which to evacuate the smoke plume as well as bodily fluids generated during laser surgery without subjecting a hospital or other permanent aspiration system to clogging and without exhausting into the environment a portion of the plume which should be first eliminated from the air. This is preferably accomplished by trapping the gas portion of the aspirated liquid in the region above the liquid in a liquid collector bag of the aspirator, and then applying a portion of the vacuum from the vacuum filter inlet to this region to remove some of the gases as they collect. The removed gases are then filtered with the plume drawn in directly by the vacuum filter assembly.

In addition, to facilitate use of the apparatus, the vacuum filtration assembly is provided with a reversible filter having a moisture absorbing cellulose portion on each end with a charcoal portion in the center. The filter is symmetrical so that the filter may be rapidly changed with a new filter inserted into the evacuator without regard to its direction.

These and other objects and advantages of the invention shall be made apparent from the accompanying drawings and the description thereof.

BRIEF DESCRIPTION OF THE DRAWINGS

The accompanying drawings, which are incorporated in and constitute a part of this specification, illustrate a preferred embodiment of the invention and, together with a general description of the invention given above, and the detailed description of a preferred embodiment given below, serve to explain the principles of the invention.

DETAILED DESCRIPTION OF THE DRAWINGS

Figure 1:
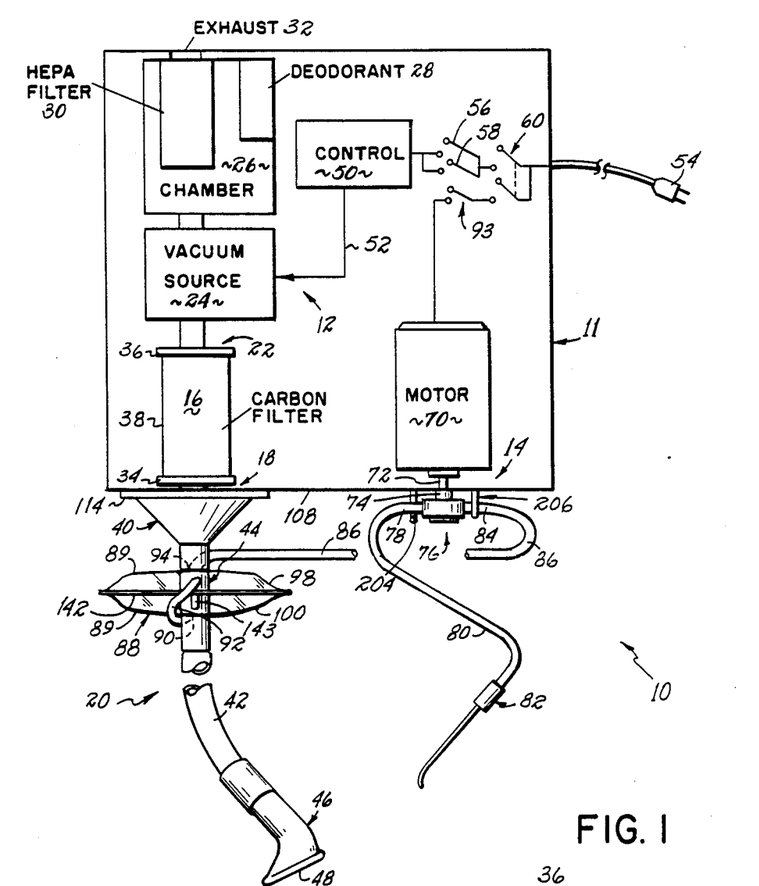
FIG. 1 is a diagrammatic view of an evacuator/aspirator system in accordance with the principles of the present invention.

With reference to FIG. 1, there is shown a diagrammatic view of a laser surgery evacuator and aspirator system 10 in accordance with the principles of the present invention. System 10 is a self-contained portable unit which may be brought into an operating room and includes associated with a single housing 11 a vacuum filter assembly 12 and an aspirator pump assembly 14. Vacuum filter assembly 12 includes a reversible cartridge filter 16 coupled at one end 18 to an evacuator hose assembly 20 and at its opposite end 22 to a source of vacuum 24 such as a vacuum motor or the like as is conventional. Vacuum source 24 exhausts into a plenum or chamber 26 in which are situated deodorant canister 28 and HEPA (high efficiency particulate absorbing) filter 30. HEPA filter 30 is situated in chamber 26 so that exhaust 32 communicates with chamber 26 through filter 30 whereby to finally filter air passing out of system 10 and into the environment exteriorly of housing 11.

Figure 5:
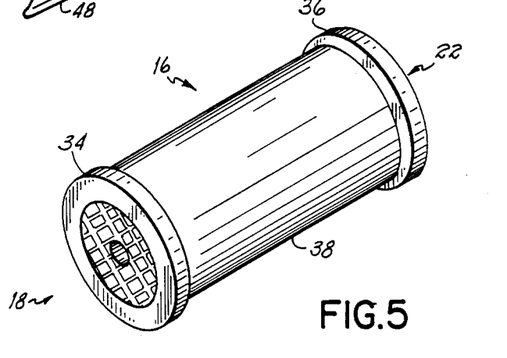
FIG. 5 is a perspective view of a reversible cartridge filter of the vacuum filter assembly in accordance with the principles of the present invention.

Cartridge filter 16 includes identical cylindrical cellulose moisture absorbing filters 34, 36 at each end 18, 22, respectively, and an intermediate cylindrical portion 38 comprised primarily of activated charcoal (see FIG. 5), whereby filter 16 may be situated with either end 18, 22 coupled to evacuator hose assembly 20, i.e., cartridge filter 16 is reversible as will be discussed in more detail hereafter.

Evacuator hose assembly 20 includes a vacuum concentrator cone 40 to couple the smaller approximately one inch cross-section of evacuator hose 42 to the larger cross-section of filter cartridge 16. Preferably, evacuator hose 42 is connected to cone 40 through a coupler piece 44 for purposes to be described hereafter. Hose 42 has attached at its remote end a nozzle 46. Nozzle 46 is a sterile nozzle of either disposable or reusable type and is configured with a small hood shaped inlet 48 to suck in gases and smoke-like components of the plume emitted during a laser surgical procedure at a surgical or operative site (not shown).

The intake of nozzle 46 is principally a gas which includes smoke and vapors from the plume and may include offensive or contaminating gases and moisture. During a laser surgical operation, vacuum source 24 will cause plume to be sucked into inlet 48 of nozzle 46 and through hose 42, coupling 44, and cone 40 and into cartridge filter 16 for first stage filtering. Moisture filter 34 of cartridge filter 16 will remove substantial moisture from the plume sucked into filter 16 and the activated carbon portion 38 thereof will remove organic gases and thus a major part of the odor, from the entering plume. The first stage filtered plume will be exhausted through vacuum source 24 into plenum 26 whereat deodorizing canister 28 releases chemical deodorant into chamber 26 to disinfect and deodorize gas passing therethrough. The deodorized gas is then passed out of chamber 26 through HEPA filter 30 which is positioned over exhaust 32 of plenum 26 so that all exiting gas passes through it before venting to the atmosphere of the operating room (not shown). HEPA filter 30 is designed to trap particulate matter as small as 0.3 microns in size to remove microscopic contaminants, including bacteria from the air before it is discharged through exhaust 32 into the environment such as the operating room. Accordingly, the plume from the laser surgical operation passing through filter 16 and HEPA filter 30, with the assistance of deodorant canister 28, will pass out of exhaust 32 in a purified and acceptable form.

Vacuum source 24 may be a variable speed motor as is known. Control 50 may be used to provide a control signal 52 to vacuum source 24 to vary the motor speed, i.e., to vary the vacuum through hose 42. Control 50 may be a rheostat or other variable energization device as is well understood. Control 50 is coupled to a plug body 54 via either of parallel switches 56, 58 and on/off switch 60. On/off switch 60 turns power to system 10 on and off when plug body 54 is coupled to a source of power (not shown). When switch 60 is in the on position, (switch 60 is shown in the off position in FIG. 1), activation of either switch 56 or 58 to the closed position (switches 56, 58 are shown in the open position in FIG. 1), will energize source 24 in accordance with the setting of control 50. Switch 56 may be mounted to the housing 11 of system 10 and switch 58 may be a remote or auxiliary foot switch 64, for example (see FIG. 2).

Turning to aspirator pump assembly 14, associated with housing 11 is motor 70 which provides the driving force for aspirator pump assembly 14. Motor 70 is affixed interiorly of housing 11 with its rotating shaft 72 extending outwardly from housing 11 whereat to be received on the shaft 74 of disposable impeller pump unit 76 (see FIG. 4). Pump unit 76 includes an inlet 78 coupled via an aspirator tube 80 approximately 5/16 inch in diameter, to a nozzle 82 through which liquids are sucked from the operating site (not shown). Pump unit 76 further includes an outlet 84 coupled via another 5/16 inch diameter tube section 86 to an aspirant container 88, such as a bag. Container 88 is vented at 90 which in a preferred embodiment is coupled to evacuator hose assembly 20 via tube portion 92 as will be discussed hereafter.

Motor 70 may be energized by activation of switch 93 in series with switch 60. When motor 70 is energized, shaft 72 will rotate causing rotation of impeller pump unit 76 to draw liquid from the operative site through nozzle 82 and discharge same into container 88.

As thus described, the present invention provides a system 10 which includes both a vacuum filter assembly 12 for laser surgery plume evacuation and an aspirator pump assembly 14 for fluid removal during that surgery, all associated into a single, portable unit. The system 10 thus provides all evacuation and aspiration needs in one easily transported and powered unit.

In accordance with a further and important aspect of the invention, plume drawn off by the aspirator pump assembly 14 is not exhausted into the environment without being first treated by vacuum filter assembly 12. To this end, the venting of the container 88 is by way of tube 92 which couples container 88 to vacuum hose assembly 20 at vacuum coupling 44 whereby to draw a vacuum on container 88 by which plume draw-off not retained in container 88 will be driven into vacuum filter assembly 12 for treatment. In a preferred embodiment, container 88 is an expandable bag ported at 94 to aspirator tube portion 86 and at 90 to vent tube 92 with an intermediate filter wall 96 therebetween.

As impeller pump 76 is operated by motor 70, fluids will be drawn into nozzle 82, through tube 80 where they will enter pump 76 through pump inlet 78. Fluids will then be expelled from pump unit 76 through pump outlet 84 via tube 86 where they will collect in collector bag 88. The fluids so drawn will include primarily liquid from the operating site, but in addition, will include a certain amount of gas including not only air which is present above the operating site but also a portion of the plume of the laser surgical procedure. This portion of the plume (the plume draw off) will also be transported into bag 88. To this end, bag 88 has a porous membrane 96 separating it into two halves, an inlet half 98, with which the bag inlet 94 communicates, and an outlet half 100 to which tube section 92 is connected. Membrane 96 impedes the direct flow of gas and liquid from the inlet 94 causing the liquid to drain to the bottom of bag 88. Some of the gases pass through membrane 96 where they are sucked into tube 92 and from there into vacuum filter assembly 12. Bag 88 is preferably comprised of two generally flexible and transparent plastic outer walls 89. Each of walls 89 are multi-layered clear film consisting generally of a layer of polyethylene terephthalate and a layer of ethylene vinyl acetate/polyethylene. Walls 89 are joined along their periphery by heat sealing or the like. An inner filter wall 96 is heat sealed between walls 89 at the perimeter thereof as well. Wall 96 is a generally translucent sheet of spun bonded olefin filtration media made from 100% high density polyethylene fibers and sold by DuPont Company under the trademark Tyvek. Any plume draw-off not retained in inlet half 98 by membrane 96 is supplied to vacuum filter assembly 12. Thus there is provided an aspirator feedback path between aspirator pump assembly 14 and vacuum filter assembly 12 whereby plume draw off may be treated before it is exhausted.

Figure 2:
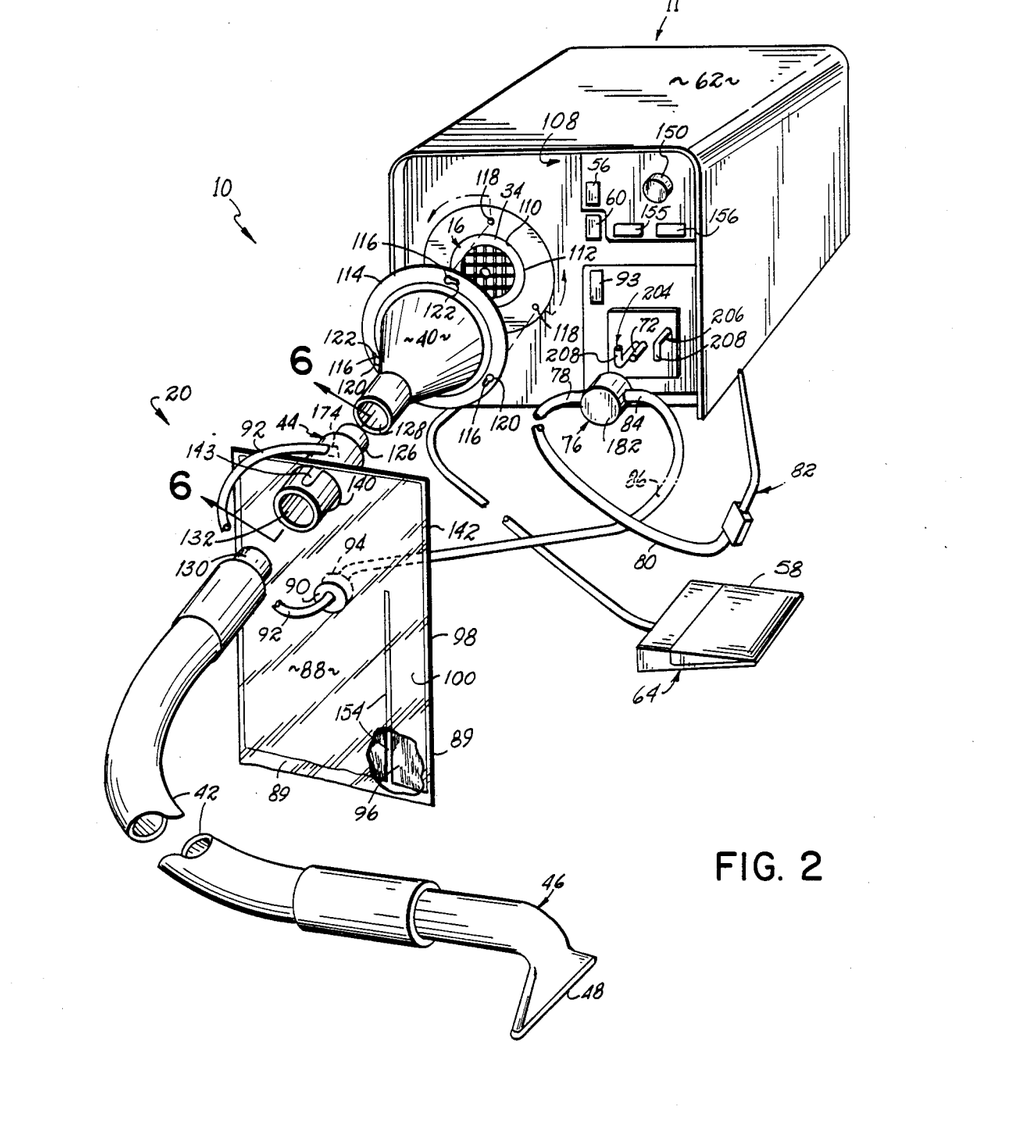
FIG. 2 is an exploded, perspective view from the front of a preferred embodiment of the present invention.
Figure 3:
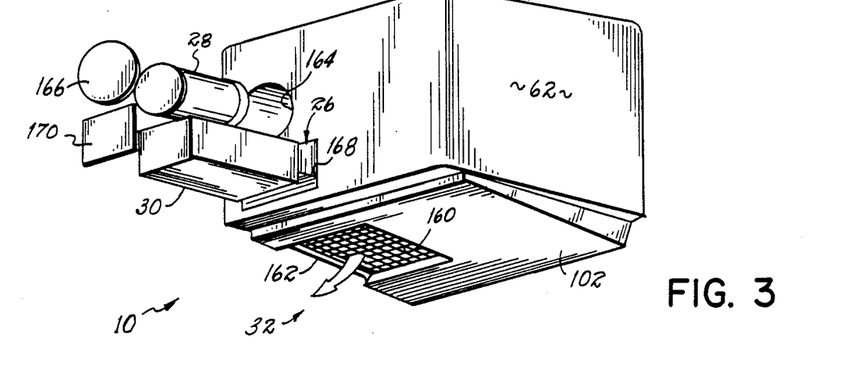
FIG. 3 is an exploded perspective view from the back and bottom of the embodiment of FIG. 2.

With reference to FIGS. 2-5, a preferred embodiment of system 10 is described. In particular, FIG. 2 is an exploded, perspective view from the front of a preferred embodiment of the system 10 according to the principles of the present invention. System 10 is preferably comprised of a single housing 11 having a stainless steel upper housing 62 supported on a molded plastic base 102 as will be described (FIG. 3). Upper housing 62 includes a front panel 108 provided with an aperture 110 coupled to a cylindrical well 112. Cartridge filter 16 is received in well 112 through aperture 110 such that the back end 22 of filter 16 abuts the back wall (not shown) of well 112 and which is coupled to vacuum source 24 within housing 11. Vacuum concentrator cone 40 couples to front panel 108 so as to secure cartridge filter 16 within cavity 112.

Concentrator cone 40 includes a bottom circular flange 114 having an outer diameter larger than the diameter of cavity 112 and an inner diameter less than the diameter of cartridge filter 16. Thus, when cone 40 is secured to front panel 108, flange 114 will hold cartridge filter 16 within cavity 112. Circular mounting flange 114 has three slots 116 formed therethrough to mate with corresponding headed pins 118 extending from front panel 108 about cavity 112. Cone 40 is secured to front panel 108 by inserting headed pins 118 through large openings 120 of slots 116 and then rotating cone 40 counterclockwise so that the terminus portions 122 of slots 116 pass under the heads of pins 118.

Evacuator hose 42 is preferably coupled to cone 40 via evacuator hose coupler 44 having a male end 126 adapted to fit within female opening 128 of cone 40. Similarly, male end 130 of hose 42 is sized to fit within female opening 132 of coupling 44. In the preferred embodiment, aspirant container 88 is secured to system 10 by cooperation of bag 88 and evacuator hose coupler 44. As may be seen in FIG. 2, an aperture 140 is formed in top portion 142 of bag 88. Aperture 140 is sized to receive evacuator coupler 44 therethrough and includes a depending tab 143 to frictionally engage same. Aperture 140 is sealed about its periphery by heat sealing as done to seal walls 89 together. Hose 42 may be coupled to cone 40 through coupler 44 while coupler 44 serves to suspend aspirant container 88 from evacuator hose assembly 20. Thus, the collector bag 88 is visible from the front of the system 10 and is also suspended to system 10 without interfering with use of system 10 and without requiring an extra support surface to hold the aspirant container or prevent it from accidentally tipping over.

Bag 88 may be suspended from the unit so that inlet half 98 is visible from the front of the unit. Alternatively, bag 88 may be suspended as shown with outlet half 100 facing forward so that fluid build-up in bag 88 is not readily visible. This orientation is desirable where patients are awake during the laser surgical procedure. Under such circumstances, however, attendants in the operating room will not know when bag 88 is becoming full. To this end, a vertical stripe or sight slot 154 is formed in membrane 96 by temporarily applying a teflon-coated nichrome heater wire thereto before sealing membrane 96 in bag 88. Upon application of the heater wire, the area of membrane 96 below the wire will become transparent to provide a sight slot 154 therein. Slot 154 may be marked with volume graduations (not shown) applied, for example, to wall 89 adjacent outlet half 100 and overlying slot 154. Thus, as fluid builds up in inlet half 98, the fluid will appear at ever-increasing levels within sight slot 154 much like a thermometer or the like to facilitate monitoring the contents of bag 88.

As also shown in FIG. 2, on/off switch 60, vacuum filter assembly switch 56, control knob 150 (coupled to control 50 to vary control signal 52), and motor switch 93 may be mounted directly to front panel 108. Also mounted on the front of the panel 108 are a pair of indicator lights 155 and 156 to indicate the clogged condition of the filters 16 and 30, respectively. These are activated by conventional differential pressure detection (not shown) which detect excess pressure drop across the filters 16 and 30.

Referring to FIG. 3, there is shown an exploded, perspective view from the back and bottom of system 10 showing that upper housing 62 is supported on a molded plastic base 102. Base 102 may be set upon a cart, table or counter or other support surface (not shown). As seen in FIG. 3, exhaust 32 of system 10 projects downwardly from system 10 so as to exhaust through a screen 160 in molded plastic base 102. To this end, molded plastic base 102 provides an offset support 162 so that when system 10 is set on a support surface (not shown), vent 32 is supported thereabove to permit an exhaust ventilation space therebelow so as to not interfere with exhausting of treated plume through exhaust 32. Also shown in FIG. 3 is aperture 164 through which deodorant canister 28 may be inserted and removed from system 10. Aperture 164 is preferably sealed by a cover 166. Further HEPA filter 30 may be inserted or removed from plenum 26 through rear access aperture 168 which also includes a cover 170 to seal aperture 168.

Figure 6:
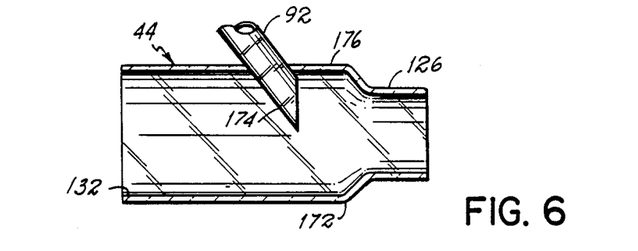
FIG. 6 is a cross-sectional view along line 6—6 of FIG. 2 of the evacuator hose coupler.

In accordance with the present invention, and as mentioned, the aspirator pump assembly 14 has a feedback path to couple plume draw off into vacuum filter assembly 12 via tube 92. In a preferred embodiment, and as seen in FIG. 6, tube 92 is connected to inlet 172 of hose coupler 44 such that end 174 of tube 92 enters through a side wall 176 of coupler 44 and extends towards the narrowed male end 126 so that as plume is drawn through coupler 44 from left to right as seen in FIG. 6, it will not impinge the interior of tube 92.

Figure 4:
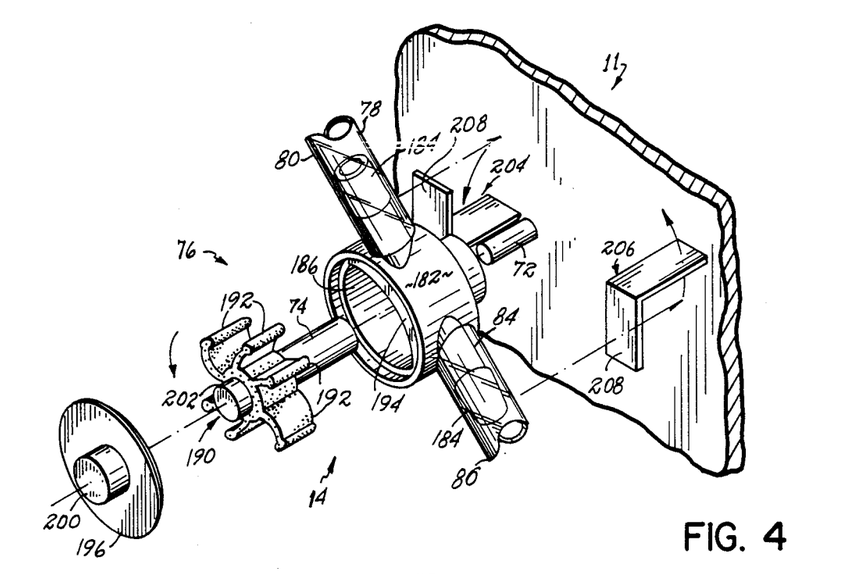
FIG. 4 is an exploded, perspective view of a portion of a preferred aspirator pump assembly for purposes of explaining the principles of the present invention.

With reference to FIGS. 2 and 4, a further aspect of the present invention will be described. In particular, as previously mentioned, aspirator pump assembly 14 includes disposable impeller pump unit 76. Pump unit 76 is preferably comprised of a plastic housing 182 to which are integrally formed plastic inlet 78 and plastic outlet 84 to be coupled to tubes 80 and 86, respectively. Inlet and outlet 78 and 84, respectively, include enlarged plastic sections 184 at their terminal ends to frictionally engage the interior of tubes 80 and 86, respectively. Housing 182 has a generally cylindrical exterior and a generally elliptical or eccentric interior pump chamber 186 as is conventional in an impeller pump unit.

Mounted within housing 182 is impeller blade assembly 190. Impeller blade assembly 190 includes rubber impeller veins 192 mounted to brass shaft 74. The rightwardly end of shaft 74 as seen in FIG. 4 is hollowed out (not shown) and extends out of housing 182 to be slidably received over and form a tight slip fit with rotating shaft 72 of motor 70. Shaft 74 is centered relative the exterior of housing 182 but is offset relative the center of the eccentric interior 186 of shell 182 so that as shaft 74 rotates, impeller veins 192 will expand and compress to draw fluid in through inlet 78 and expel it out of outlet 84 as is conventional. That is, pump chamber 186 has an inwardly displaced wall 194 on one side thereof to compress impeller veins 192 to force fluid out of outlet 84 and to expand impeller veins 192 to draw fluid into the inlet 78 as impeller veins 192 rotate counter-clockwise as seen in FIG. 4. Housing 182 is covered by a cap 196 which seals elliptical pump chamber 186 defined within housing 182. A recess 200 in cap 196 receives the outer end 202 of shaft 74 to help support it.

Assembled pump 76 slips onto shaft 72 and connects to tubes 80 and 86. Then, as motor 70 is actuated to drive impeller pump unit 76, unit 76 turns counterclockwise as seen in FIG. 4 until tubes 80 and 86 on the inlet and outlet fittings or conduits 78 and 84 rest against a pair of clips 204 and 206 on front panel 108. Clips 204, 206 hold pump 76 against further rotation. Clips 204, 206 are preferably L-shaped so that they have an exterior wall portion 208 generally parallel front panel 108 of upper housing 62 so as to define pump unit conduit receiver zones which accept conduits 78, 84 and prevent impeller pump unit 76 from being pulled away from system 10 inadvertently or during use.

By cooperation of inlet and outlet 78 and 84, respectively, and clips 204 and 206, impeller pump unit 76 may be readily and easily placed onto and removed from system 10. This arrangement provides a very quick and efficient means for changing impeller pump unit 76 without a requirement to manipulate any clips or fasteners to secure pump unit 76 to system 10. In this way, impeller pump unit 76 may be made to be disposable so that it can be replaced between operations thus improving sterility management. Further, no portion of aspirator pump assembly 14 which contacts bodily fluids sucked in through nozzle 82 is permanently secured to system 10. Thus, such portions of aspirator pump assembly 14 which are intended to come into contact with bodily fluids may be readily removed and either replaced or sterilized to facilitate sterility management.

By virtue of the foregoing, there is provided a system 10 which not only provides laser surgery plume evacuation and liquid aspiration in one self-contained unit, but further provides such a system in which feedback of plume drawn off by the aspirant assembly may be treated before being exhausted to the environment without the addition of further filtration or vacuum systems and without necessitating use of a hospital or separate aspiration system which may be subject to clogging or damage or expulsion of plume contaminants into the environment. Still further, the present invention thus provides an evacuator/aspirant system for laser surgery in which those components of the system which are intended to come into contact with bodily fluids may be readily disposed of and replaced or removed from the system 10 and sterilized prior to their next use. Still further, in the event filter 16 becomes clogged, it may be readily replaced by removing cone 40, withdrawing filter 16 and replacing it with a new cartridge filter 16. Due to the reversible construction of cartridge filter 16, attendants in the operating room need not concern themselves with the proper orientation of cartridge filter 16 as either forward or reverse insertion into well 112 will result in a humidity filter 34 or 36 being placed first in line with the evacuator hose so as to remove moisture from plume sucked in through hose 42. This is important because removal of moisture is preferred to reduce the likelihood of fouling or clogging the activated carbon portion of filter 16 and/or HEPA filter 30 thereby reducing their useful life. Also, because filter 16 may be so readily replaced, and indeed because impeller pump unit 76 is easily mountable to system 10, in the event replacement of filter 16 or impeller pump unit 76 is necessary during a surgical procedure, only a minimum of down time will be necessary to make that change and without requiring undue attention from attendants assisting the surgeon.

While the present invention has been illustrated by description of a preferred embodiment and while the preferred embodiment has been described in considerable detail, it is not the intention to restrict or in any way limit the scope of the appended claims to such detail. For example, housing 11 may be comprised of multiple compartments and housing sections joined together as if they were one housing. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of the general inventive concept.

What is claimed is:

1. A method of evacuating and aspirating a laser surgery site comprising:
   evacuating through a vacuum filter assembly plume generated during a laser surgical procedure;
   aspirating through an aspirator pump assembly fluid containing liquid and plume generated during the laser surgical procedure; and
   ventilating at least a portion of plume aspirated into said aspirator pump assembly to said vacuum filter assembly to pass such aspirated plume portion through said vacuum filter assembly.

2. The method of claim 1 wherein said ventilating includes
   collecting in an aspirant collector fluid and plume aspirated through said aspirator pump assembly; and
   venting said aspirant container to said vacuum filter assembly to pass through said vacuum filter assembly plume drawn off by said aspirator pump assembly and not retained in said aspirant collector.

3. The method of claim 1 further comprising separating a portion of the aspirated plume from the aspirated liquid before ventilating the aspirated plume portion into said aspirator pump assembly.

4. A method of evacuating and aspirating a laser surgery site comprising:
   evacuating through a vacuum filter assembly plume generated during a laser surgical procedure and exhausting cleaned air therefrom into an operating room environment;

aspirating through an aspirator pump assembly fluid containing liquid and plume generated during the laser surgical procedure;

feeding from said aspirator pump assembly to said vacuum filter assembly gaseous components of plume aspirated into said aspirator assembly; and cleaning in the vacuum filter assembly said gaseous plume components and exhausting the cleaned components into said operating room environment.

5. The method of claim 4 further comprising collecting the fluid containing liquid and plume aspirated through said aspirator assembly before feeding said gaseous plume components into said vacuum filter assembly.

6. The method of claim 5 further comprising venting gaseous plume components of the collected fluid into said filter assembly.

7. A laser surgery evacuator/aspirator comprising:
a portable housing positionable in the environment of an operating room near an operating site;
a vacuum filter assembly associated with said housing, said vacuum filter assembly including vacuum means and means for coupling to an outlet end of an evacuator vacuum hose which has an inlet end positionable adjacent an operating site for evacuating through the hose and said vacuum filter assembly plume generated during a laser surgical procedure;
an aspirator pump assembly associated with said housing, said aspirator pump assembly including motive means and means for coupling to a suction means which has an inlet end positionable adjacent the operating site for aspirating through the suction means liquid generated during the laser surgical procedure; and
power connecting means associated with said housing for providing power to both said vacuum means of said filter assembly and said motive means of said aspirator pump assembly whereby plume and liquid generated during laser surgery may be removed from the operating site without the need for a separate aspirator system or a separate power source therefor.

8. The laser surgery evacuator/aspirator of claim 7 wherein said motive means of said aspirator pump assembly includes:
an aspirator pump motor situated within said housing and having a rotatable shaft extending out of said housing for selectively coupling to a removable aspirant pump unit forming part of the aspiration suction means.

9. In combination with the laser surgery evacuator/aspirator of claim 7 wherein said motive means of said aspirator pump assembly includes an aspirator pump motor situated within said housing and having a rotatable shaft extending out of said housing, suction means for aspirating therethrough liquid generated during the laser surgical procedure, said suction means including:
a disposable impeller pump unit having inlet means for coupling to an aspirator tube having an inlet end positionable adjacent the operating site, said pump unit having a shaft being selectively couplable to said motor rotatable shaft.

10. The laser surgery evacuator/aspirator of claim 7 wherein said vacuum filter assembly includes:
at least one filter having a central section of filtering material and a pair of moisture sections axially spaced from each other on opposite sides of said central section, each capable of serving as either an inlet or outlet, said filter being configured symmetrically about a central section so that said filter is connectable in an orientation with either of said moisture sections toward said means for coupling to an outlet end of the evacuator vacuum hose.

11. The laser surgery evacuator/aspirator of claim 7, said aspirator pump assembly further including a pump unit connected to and being drivable by said motive means and supporting said means for coupling to the suction means, said aspirator pump assembly further including an aspirant collector coupled to said pump unit, whereby liquid aspirated through the suction means will collect in the aspirant collector, said aspirant collector including means for ventilating into said vacuum filter assembly plume drawn in by the suction means with the aspirated liquid whereby to pass such drawn in plume through said vacuum filter assembly.

12. The laser surgery evacuator/aspirator of claim 11 wherein said vacuum filter assembly further has means for supporting said aspirant collector thereon.

13. A laser surgery evacuator/aspirator comprising:
a housing positionable in the environment of an operating room near an operating site;
a vacuum filter assembly associated with said housing, said vacuum filter assembly having vacuum means and means for coupling to an evacuator vacuum hose which has an inlet end positionable adjacent an operating site for evacuating plume generated during the laser surgical procedure through said hose and said vacuum filter assembly;
an aspirator pump motor situated within said housing, said aspirator pump motor having a rotatable shaft extending therefrom to receive a removable aspirant pump unit thereon; and
fixed means carried by said housing for cooperating with the removable aspirator pump unit to hold the removable aspirator pump unit to said rotatable shaft; and
power connecting means associated with said housing for providing power to both said vacuum means of said vacuum filter assembly and said aspirator pump motor whereby plume and liquid generated during laser surgery may be removed from the operating site without the need for a separate motive force for the aspirator pump or a separate power source therefor.

14. The laser surgery evacuator/aspirator of claim 13 wherein said fixed means includes a hook shaped member projecting from said housing to define a pump unit conduit receiver zone.

15. The laser surgery evacuator/aspirator of claim 13 wherein said housing is portable.

16. A laser surgery evacuator/aspirator comprising:
a housing positionable in the environment of an operating room near an operating site;
a vacuum filter assembly carried by said housing, said vacuum filter assembly having vacuum means and an evacuator vacuum inlet hose coupled to said vacuum means, said inlet hose having an inlet end positionable adjacent an operating site for evacuating therethrough plume generated during a laser surgical procedure, said vacuum filter assembly further having filter means connected in series with said evacuator vacuum inlet hose and vacuum means for drawing plume through said inlet hose and said filter means to a clean air exhaust, said exhaust communicating with said operating room environment;

an aspirator pump assembly carried by said housing and having an aspirator inlet hose with an inlet end positionable adjacent the operating site for aspirating therethrough liquid generated during the laser surgical procedure, said aspirator pump assembly further having motive means for drawing liquid through said aspirator inlet hose; and feed means coupled between said aspirator pump assembly and said vacuum filter assembly for feeding, to said vacuum filter assembly from said aspirator pump assembly, at least a portion of gaseous components of the aspirated liquid drawn into said aspirator inlet hose whereby the gaseous components are cleaned by said vacuum filter assembly before being exhausted into said operating room environment.

17. The laser surgery evacuator/aspirator of claim 16 wherein said housing is portable.

18. The laser surgery evacuator/aspirator of claim 16 wherein said filter means includes:

at least one filter having a central section of filtering material and a pair of moisture sections axially spaced from each other on opposite sides of said central section, each capable of serving as either an inlet or outlet, said filter being configured symmetrically about a central section so that said filter is connectable in an orientation with either of said moisture sections toward the evacuator vacuum inlet hose.

19. The laser surgery evacuator/aspirator of claim 16, said aspirator pump assembly including an outlet, said feed means including an aspirator collector having an inlet connected to said pump assembly outlet for collecting liquid aspirated through said aspirator inlet hose.

20. The laser surgery evacuator/aspirator of claim 19 wherein said aspirator collector comprises a bag suspended from said evacuator vacuum inlet hose.

21. The laser surgery evacuator/aspirator of claim 19 wherein said feed means further includes means connecting an outlet of said aspirator collector to said evacuator vacuum inlet hose.

22. The laser surgery evacuator/aspirator of claim 21, said aspirator collector comprising a flexible wall plastic bag having a membrane dividing said bag into at least two halves, one said half communicating directly with said collection inlet, another said half communicating directly with said collection outlet, whereby the gaseous components are those that pass through said membrane from said one half to said another half.

23. The laser surgery evacuator/aspirator of claim 22, said ba being generally transparent, said membrane being generally vertically disposed and further being generally translucent, said membrane including a vertical, generally transparent slot therein.

24. The laser surgery evacuator/aspirator of claim 16 wherein said aspirator pump assembly includes:

a disposable pump removably mounted on said housing, removably connected to said motive means, and connected in series between said aspirator inlet hose and said feed means.

25. The laser surgery evacuator/aspirator of claim 24 wherein said motive means of said aspirator pump assembly includes a rotary pump motor mounted within said housing and having a rotary output shaft extending through said housing, said disposable pump having a pump body and a pump shaft rotatable in said pump body, said pump shaft being removably connectable to said motor shaft for supporting said disposable pump on said housing, said pump body having at least one abutment surface thereon; said laser surgery evacuator/aspirator further comprising:

at least one stop fixed to said housing and adjacent said motor shaft for engaging said abutment surface of said disposable pump to restrain said pump body against rotation with the rotary output shaft of said motor.

26. The laser surgery evacuator/aspirator of claim 25 wherein said pump shaft is slidable axially on said motor shaft for connection thereto and rotation therewith.

27. A laser surgery evacuator/aspirator system comprising:

a portable housing positionable in the environment of an operating room near an operating site;

a vacuum filter assembly associated with said housing and including:

a vacuum source inside said housing;

filter means inside said housing for filtering air drawn in by said vacuum source;

means for expelling filtered air out of said housing and into said operating room environment; and means communicating said vacuum source to an evacuator inlet;

an aspirator pump assembly comprising:

a motor inside said housing and having a rotatable shaft extending out of said housing;

a disposable impeller pump unit having a pump body, said pump unit having inlet and outlet arms extending from said pump body, said pump unit further having a shaft extending from said pump body generally perpendicular said arms and slidably received on said rotatable motor shaft for rotation therewith;

an aspirator tube having a nozzle end positionable adjacent the operating site for sucking therethrough liquid and drawn off plume generated during a laser surgical operating procedure, said tube having another end coupled to said pump unit inlet arm;

an evacuator hose having a nozzle end positionable adjacent the operating site for evacuating therethrough plume generated during the laser surgical procedure, said hose having another end coupled to said evacuator inlet;

an aspirant collector coupled to said pump unit outlet arm for collecting liquid and drawn off plume sucked in through said aspirator tube, said aspirant collector having a vent;

coupling means coupling said vent of said aspirant collector to said evacuator hose for drawing into said vacuum filter assembly drawn off plume sucked in through said aspirator tube and not retained in said aspirant collector whereby said drawn off plume is not exhausted unfiltered into said operating room environment.

28. The laser surgery evacuator/aspirator of claim 27, said coupling means has an outlet opening positioned within said evacuation hose and facing downstream in the direction of flow within said hose.

29. The laser surgery evacuator/aspirator of claim 27 wherein said collector includes a collector bag supported by and depending from said evacuator hose.

30. The laser surgery evacuator/aspirator of claim 27, said aspirant collector comprising:

a flexible-wall plastic bag having a membrane dividing said bag into at least two halves, one said half communicating directly with said pump unit outlet arm, another said half communicating directly with said vent.

31. The laser surgery evacuator/aspirator of claim 30, said bag being generally transparent, said membrane being generally vertically disposed and further being generally translucent, said membrane including a vertical, generally transparent slot therein.

* * * * *

UNITED STATES PATENT AND TRADEMARK OFFICE
CERTIFICATE OF CORRECTION

PATENT NO. : 4,963,134

DATED : October 16, 1990

INVENTOR(S) : Frank A. Backscheider and Paul Rogers

It is certified that error appears in the above-identified patent and that said Letters Patent is hereby corrected as shown below:

Claim 23, Col. 13, line 53, "ba" should be --bag--.

Signed and Sealed this

Twelfth Day of May, 1992

Attest:

DOUGLAS B. COMER

*Attesting Officer*   *Acting Commissioner of Patents and Trademarks*